US010273502B2

(12) United States Patent
Truran et al.

(10) Patent No.: US 10,273,502 B2
(45) Date of Patent: *Apr. 30, 2019

(54) VIRUS PURIFICATION (71) Applicant: Oxford BioMedica (UK) Limited, Oxford (GB)

(72) Inventors: Richard Truran, Oxford (GB); Robert Buckley, Oxford (GB); Pippa Radcliffe, Oxford (GB); James Miskin, Oxford (GB); Kyriacos Mitrophanous, Oxford (GB)

(73) Assignee: Oxford BioMedica (UK) Limited, Oxford (GB)

(*) Notice: Subject to any disclaimer, the term of this patent is extended or adjusted under 35 U.S.C. 154(b) by 43 days.

This patent is subject to a terminal disclaimer.

(21) Appl. No.: 14/852,735

(22) Filed: Sep. 14, 2015

(65) Prior Publication Data
US 2017/0073702 A1 Mar. 16, 2017
US 2017/0175135 A9 Jun. 22, 2017

Related U.S. Application Data (63) Continuation of application No. 12/487,215, filed on Jun. 18, 2009, now Pat. No. 9,169,491.

(60) Provisional application No. 61/073,685, filed on Jun. 18, 2008.

(51) Int. Cl.
*C12N 7/02* (2006.01)
*C12N 15/00* (2006.01)
*C12N 15/86* (2006.01)
*A61K 48/00* (2006.01)
*A61K 38/17* (2006.01)

(52) U.S. Cl.
CPC ............ *C12N 15/86* (2013.01); *A61K 38/177* (2013.01); *A61K 38/1719* (2013.01); *C12N 2740/15043* (2013.01); *C12N 2740/15051* (2013.01)

(58) Field of Classification Search
None
See application file for complete search history.

(56) References Cited

U.S. PATENT DOCUMENTS 6,214,574 B1 * 4/2001 Kopf .................. B01D 61/32
435/170
2009/0191155 A1 * 7/2009 Williams ............. A61K 48/005
424/93.2

FOREIGN PATENT DOCUMENTS

WO  WO 2006108707 A1 * 10/2006 ............... C12N 7/00
WO  WO 2008/065430        6/2008
WO  WO 2008065430 A2 *  6/2008 ............. C12N 15/85

OTHER PUBLICATIONS

Hashimoto, et al., Lentiviral gene replacement therapy of retinas in a mouse model for Usher syndrome type 1B, Gene Therapy 14:584-594 (2007).
Cheryan M., Ultrafiltration and Microfiltration Handbook; Technomic Publishing Company, Inc. (Lancaster, PA), 1998.
Dupont F., Large Scale Manufacturing of a Lentiviral Vector (ProSavin®) for Phase I/II Clinical Trial. 2008; (Presented at the CONSERT Labcourse, Evry/F, Jun. 29-Jul. 1, 2008).
Meltzer T.H., Modus of Filtration, Adv. Biochem. Engin./Biotechnol. 98:27-71, 2006.
Merten O. et al., Production of lentiviral vectors, Molecular Ther.—Meth. Clin. Devel. 3:16017, doi:10.1038/mtm.2016.17, 2016.
Slepushkin V. et al., Large-scale Purification of a Lentiviral Vector by Size Exclusion Chromatography or Mustang Q Ion Exchange Capsule, BioProcessing J. 2:89-95, 2003.
Transfiguracion J. et al., High yield purification of functional baculovirus vectors by size exclusion chromatography, J. Virolog. Meth. 142:21-28, 2007.
US Dept. of Health and Human Services/FDA, Guidance for Industry: Sterile Drug Products Produced by Aseptic Processing—Current Good Manufacturing Practice, 2004.

* cited by examiner

Primary Examiner — Christopher M Babic
Assistant Examiner — Kimberly A. Aron
(74) Attorney, Agent, or Firm — Grimes & Yvon LLP (57) ABSTRACT A process for producing a retroviral or lentiviral vector formulation comprising a filter-sterilisation step wherein the filter-sterilisation step is not the final step in the purification process.

21 Claims, 2 Drawing Sheets

Figure 1: Viral vector manufacturing process

Figure 1 (continued): Viral vector manufacturing process (continued)

VIRUS PURIFICATION

INCORPORATION BY REFERENCE

This application claims the benefit of U.S. application Ser. No. 12/487,215, filed Jun. 18, 2009, and of U.S. Provisional Application No. 61/073,685, filed Jun. 18, 2008. The above applications, together with each document cited therein, and each of the documents referenced or cited in documents cited therein, is hereby incorporated herein by reference. Additionally, each document cited in this text ("application cited documents") and each document cited or referenced in each of the application cited documents, and any manufacturer's specifications, data sheets, descriptions, product literature, instructions and the like for any products mentioned herein or in herein cited documents or in documents cited in herein cited documents, is hereby incorporated herein by reference. None of the documents incorporated by reference into this text is admitted to be prior art with respect to the present invention, but, documents incorporated by reference into this text may be employed in the practice of the invention.

FIELD OF THE INVENTION

The present invention relates to improved methods of retroviral vector production and purification.

BACKGROUND TO THE INVENTION

The success of gene therapy techniques depends on the ability to achieve sufficient expression of transferred genes in a manner safe to humans. Retroviruses are often used as a delivery system (otherwise expressed as a delivery vehicle or delivery vector) for inter alia the transfer of a nucleotide of interest (NOI), or a plurality of NOIs, to one or more sites of interest. There has also been considerable interest in the development of lentiviral vector systems because lentiviruses are able to infect non-dividing cells (Lewis & Emerman (1993) J. Virol. 68:510). In addition lentiviral vectors enable very stable long-term expression of the gene of interest. This has been shown to be at least one year for transduced rat neuronal cells in vivo (Bienemann et al. (2003) Mol. Ther. 5:588).

The vector purification process is an important step in clinical gene transfer therapies, and is directly linked to safety and efficacy in terms of purity and titre. In most small-scale experimental applications, vectors can be concentrated and purified by relatively simple methods using centrifugation techniques. However, scaling up the purification methods for large-scale production for clinical use represents a major challenge. In particular, when considering production of vector for human use, additional steps such as sterilisation by filtration must be taken to ensure the purity and safety of the vector preparation.

Vector preparation methods generally comprise obtaining vector from cells making vector either stably or transiently and purifying the viral vector using, for example, chromatography. In industrial processes, the final step is the sterilisation step and at least one ultrafiltration step is usually used prior to the sterilisation step so as to concentrate the viral vector and/or to exchange the buffer in which the viral vector is kept.

Several publications describe the purification of viruses from cells, mostly discussing the use of specific chromatographic matrices for purification of the virus from a cell lysate. For example, U.S. Pat. Nos. 6,261,823 and 5,661,023 disclose methods encompassing the use of anion exchange resin alone while U.S. Pat. No. 5,837,520 discloses a sequential combination of anion exchange followed by affinity chromatography. Yamada et al. shows that lentivirus vector purification using anion exchange HPLC leads to improved gene transfer (Yamada et al. (2003) Biotechniques 34(5):1074-8, 1080).

There remains a need for a large-scale retroviral vector purification method that yields pure product while preserving high titres. The present invention addresses this need.

SUMMARY OF THE INVENTION

We have shown that, unexpectedly, improved processes for producing retroviral and lentiviral vector formulations can be achieved when a filter-sterilisation step is not the final step in the production process. In particular, we have found that a filter-sterilisation step which is performed subsequently to a concentration step (e.g. by ultrafiltration), results in a considerable loss of viral vector titre. This was surprising as the diameter of retroviral particles is in the range 80-120 nm and they should easily pass through the pores of a sterilising filter; indeed this is the case for vector-containing cell culture supernatants which are routinely filtered with no loss of functional titre observed. It was therefore not clear why, once the vector preparation had been processed it was no longer possible to filter sterilize the preparation without loss of recovery.

Moreover, we have surprisingly found that increased vector particle yields can be obtained if the final concentration step is performed after the filter-sterilisation step. This is contrary to established viral production processes wherein concentration steps are traditionally performed prior to the filter-sterilisation step. We have also found that maintaining a suitable vector particle concentration, for example by diluting a vector particle preparation, prior to filter-sterilisation, can also improve vector particle yields. It is surprising that lowering the vector particle concentration during some stages of the process can actually lead ultimately to improved product yield.

It will be appreciated that lower dose formulations may be produced by aseptically diluting the formulation produced by the process of the present invention.

The production process of the present invention is preferably a large scale-process for producing clinical grade formulations that are suitable for administration to humans as therapeutics.

The retroviral and lentiviral vector formulations described herein are preferably suitable for administration to humans as therapeutics.

According to a first aspect of the present invention there is provided a process for producing a retroviral or lentiviral vector formulation comprising a filter-sterilisation step wherein the filter-sterilisation step is not the final step in the production process.

Preferably the retroviral vector is a lentiviral vector.

Preferably the filter-sterilisation step occurs prior to a concentration step.

Preferably the concentration step is the final step in the process and the filter-sterilisation step is the penultimate step in the process.

Preferably the concentration step is performed using ultrafiltration, preferably tangential flow filtration, more preferably hollow fiber ultrafiltration.

Preferably the filter-sterilisation step is performed using a sterilising filter with a maximum pore size of about 0.22 µm. In another preferred embodiment the maximum pore size is 0.2 µm.

In preferred embodiments, for optimum recovery of EIAV particles the vector concentration should be less than or equal to about $4.6 \times 10^{11}$ RNA genome copies per ml of preparation prior to filter-sterilisation. The appropriate concentration level can be achieved through controlling the vector concentration using, e.g. a dilution step, if appropriate. Thus, in one embodiment, a retroviral vector preparation is diluted prior to filter sterilisation. Thus, if a skilled worker is experiencing lower than expected recovery of vector particles, he should investigate lowering the concentration of the vector particles prior to filter-sterilisation. The appropriate titre level for optimum recovery can be determined using the techniques described below, and the Example section in particular.

According to a second aspect of the present invention there is provided a process for producing a retroviral vector formulation comprising the following steps (i) to (vi) in chronological order:
 (i) culturing cells that produce retroviral vector;
 (ii) harvesting the retroviral vector containing supernatant;
 (iii) optionally clarifying the supernatant;
 (iv) purifying the retroviral vector to give a retroviral vector preparation;
 (v) filter-sterilisation of the retroviral vector preparation; and
 (vi) concentrating the retroviral vector preparation to produce the final bulk product.

In one embodiment the process does not comprise the clarifying step (iii).

In another embodiment the process does include the clarifying step (iii).

Preferably step (vi) is performed using ultrafiltration, or tangential flow filtration, more preferably hollow fiber ultrafiltration.

Preferably the purification method in step (iv) is ion exchange chromatography, more preferably anion exchange chromatography.

Preferably the filter-sterilisation in step (v) is performed using a 0.22 µm or a 0.2 µm sterilising filter.

Preferably step (iii) is performed by filter clarification.

Preferably step (iv) is performed using a method or a combination of methods selected from chromatography, ultrafiltration/diafiltration, or centrifugation.

Preferably the chromatography method or a combination of methods is selected from ion exchange chromatography, hydrophobic interaction chromatography, size exclusion chromatography, affinity chromatography, reversed phase chromatography, and immobilized metal ion affinity chromatography.

Preferably the centrifugation method is selected from zonal centrifugation, isopycnic centrifugation and pelleting centrifugation.

Preferably the ultrafiltration/diafiltration method is selected from tangential flow diafiltration, stirred cell diafiltration and dialysis.

Preferably at least one step is included into the process of the invention to degrade nucleic acid to improve purification.

Preferably said step is nuclease treatment.

Preferably said nuclease is Benzonase® Nuclease.

Preferably a nucleic acid degradation step or steps are carried out in the process of the invention at any point or points up to and including step (iv).

Preferably the purification step (iv) of the process includes a buffer exchange step.

Preferably step (vi) of the process is performed using ultrafiltration.

Preferably the ultrafiltration comprises tangential flow filtration.

Preferably the ultrafiltration comprises hollow fiber ultrafiltration.

Preferably the filter-sterilisation in step (v) of the process is performed using a sterilising filter with a maximum pore size of about 0.22 µm.

Preferably the buffer exchange comprises exchange of the buffer used for the preceding steps with formulation buffer.

Preferably the formulation buffer is a pH buffered salt solution containing sugars.

Preferably the buffer is a TRIS-based buffer.

In one embodiment the vector particle concentration is diluted prior to filter-sterilisation.

Preferably the retroviral vector is a lentiviral vector.

More preferably the lentiviral vector is a non-primate lentiviral vector.

More preferably the lentiviral vector is derived from EIAV. When the lentiviral vector is derived from EIAV the vector concentration of the EIAV particles prior to filter-sterilisation in the vector particle preparation is less than or equal to $4.6 \times 10^{11}$ RNA genome copies per ml.

Preferably the retroviral vector comprises a nucleotide of interest (NOI).

Preferably the production processes of the invention are for producing retroviral vector formulations, wherein the retroviral vector formulation is suitable for administration to a patient. The patient may be a human or an animal. In one embodiment the retroviral vector formulation is suitable for administration to an eye of a patient. In another embodiment, the retroviral vector formulation is suitable for administration to a brain of a patient.

In some embodiments, the production processes are for producing retroviral vector formulations, wherein the retroviral vector formulation is suitable for administration to a patient by injection. In one embodiment the retroviral vector formulation is suitable for direct subretinal injection optionally following vitrectomy of the eye of a human or animal. In another embodiment the retroviral vector formulation is suitable for direct injection into the striatum of the brain of a human or animal.

In some embodiments the production processes are for producing retroviral vector formulations, wherein the retroviral vector formulation is suitable for ex vivo administration.

In other embodiments the production processes are for producing retroviral vector formulations, wherein the retroviral vector formulation is suitable for administration to a cell obtainable from a patient.

According to a fourth aspect of the invention, there is provided a retroviral vector formulation obtainable by the process of the present invention. In some embodiments the retroviral vector formulation is for use in gene therapy. There is also provided use of the retroviral vector formulation in the preparation of a medicament for gene therapy.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE FIGURES

The following detailed description, given by way of example, but not intended to limit the invention solely to the specific embodiments described, may best be understood in conjunction with the accompanying drawing, in which.

DETAILED DESCRIPTION OF THE INVENTION

Various preferred features and embodiment of the present invention will now be described by way of non-limiting examples.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis (1989) *Molecular Cloning: A Laboratory Manual, Second Edition, Books* 1-3, Cold Spring Harbor Laboratory Press; Ausubel, F. M. et al. (1995 and periodic supplements) *Current Protocols in Molecular Biology*, Ch. 9, 13, and 16, John Wiley & Sons, New York, N.Y.; B. Roe, J. Crabtree, and A. Kahn (1996) *DNA Isolation and Sequencing: Essential Techniques*, John Wiley & Sons; J. M. Polak and James O'D. McGee (1990) *In Situ Hybridization: Principles and Practice*; Oxford University Press; M. J. Gait (ed.) (1984) *Oligonucleotide Synthesis: A Practical Approach*, IRL Press; and, D. M. J. Lilley and J. E. Dahlberg (1992) *Methods of Enzymology: DNA Structure Part A: Synthesis and Physical Analysis of DNA Methods in Enzymology*, Academic Press. Roe, Simon, ed. *Protein Purification Techniques.* 2nd ed. Oxford: Oxford University Press, 2001, Sofer, Gail and Hagel, Lars. *Handbook of Process Chromatography: A Guide to Optimization, Scale-up, and Validation.* London and San Diego: Academic Press, 1997, Janson, Jan-Christer and Rydén, Lars, eds. *Protein Purification: Principles, High Resolution Methods, and Applications.* 2nd ed. New York: John Wiley & Sons, Inc., 1998, Masters, John R. W., ed. *Animal Cell Culture: A Practical Approach.* 3rd ed. Oxford: Oxford University Press, 2000. Each of these general texts is herein incorporated by reference.

Polynucleotides

Polynucleotides used in the present invention may comprise DNA or RNA sequences. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides used in the invention to reflect the codon usage of any particular host organism in which the polypeptides are to be expressed. The polynucleotides may be modified by any method available in the art. Such modifications may be carried out in order to enhance the in vivo activity or life span of polynucleotides of the invention.

Polynucleotides such as DNA polynucleotides may be produced recombinantly, synthetically, or by any means available to those of skill in the art. They may also be cloned by standard techniques.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Protein

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be obtained by addition, deletion, substitution modification replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics.

Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins used in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the transport or modulation function is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Retroviruses

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host cell. Examples of vectors used in recombinant DNA techniques include but are not limited to plasmids, chromosomes, artificial chromosomes or viruses.

The term "expression vector" means a construct capable of in vivo or in vitro/ex vivo expression.

The retroviral vector employed in the aspects of the present invention may be derived from or may be derivable from any suitable retrovirus. A large number of different retroviruses have been identified. Examples include: murine leukemia virus (MLV), human immunodeficiency virus (HIV), human T-cell leukemia virus (HTLV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "Retroviruses", Cold Spring Harbor Laboratory Press Eds: J M Coffin, S M Hughes, H E Varmus pp 758-763.

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al. 1997 (ibid).

A recombinant retroviral vector particle is capable of transducing a recipient cell with a nucleotide of interest (NOI). Once within the cell the RNA genome from the vector particle is reverse transcribed into DNA and integrated into the DNA of the recipient cell.

In a typical vector for use in the method of the present invention, at least part of one or more protein coding regions essential for replication may be removed from the virus. This makes the viral vector replication-defective. Portions of the viral genome may also be replaced by an NOI in order to generate a vector comprising an NOI which is capable of transducing a target non-dividing host cell and/or integrating its genome into a host genome.

Lentiviral Vectors

The lentiviral vector according to the present invention may be derived from or may be derivable from any suitable lentivirus.

Lentiviral vectors are part of a larger group of retroviral vectors. A detailed list of lentiviruses may be found in Coffin et al. (1997) "Retroviruses" Cold Spring Harbor Laboratory Press Eds: J M Coffin, S M Hughes, H E Varmus pp 758-763). In brief, lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

The lentivirus family differs from retroviruses in that lentiviruses have the capability to infect both dividing and non-dividing cells (Lewis et al. (1992); Lewis and Emerman (1994)). In contrast, other retroviruses—such as MLV—are unable to infect non-dividing or slowly dividing cells such as those that make up, for example, muscle, brain, lung and liver tissue.

A lentiviral vector, as used herein, is a vector which comprises at least one component part derivable from a lentivirus. Preferably, that component part is involved in the biological mechanisms by which the vector infects cells, expresses genes or is replicated.

The basic structure of retrovirus and lentivirus genomes share many common features such as a 5' LTR and a 3' LTR, between or within which are located a packaging signal to enable the genome to be packaged, a primer binding site, integration sites to enable integration into a host cell genome and gag, pol and env genes encoding the packaging components—these are polypeptides required for the assembly of viral particles. Lentiviruses have additional features, such as rev and RRE sequences in HIV, which enable the efficient export of RNA transcripts of the integrated provirus from the nucleus to the cytoplasm of an infected target cell.

In the provirus, the viral genes are flanked at both ends by regions called long terminal repeats (LTRs). The LTRs are responsible for proviral integration, and transcription. LTRs also serve as enhancer-promoter sequences and can control the expression of the viral genes.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different viruses.

In a defective lentiviral vector genome gag, pol and env may be absent or not functional. The R regions at both ends of the RNA are repeated sequences. U5 and U3 represent unique sequences at the 5' and 3' ends of the RNA genome respectively.

In a typical lentiviral vector of the present invention, at least part of one or more protein coding regions essential for replication may be removed from the virus. This makes the viral vector replication-defective. Portions of the viral genome may also be replaced by an NOI in order to generate a vector comprising an NOI which is capable of transducing a target non-dividing host cell and/or integrating its genome into a host genome.

In one embodiment the retroviral vectors are non-integrating vectors as described in WO 2007/071994.

In a further embodiment the vectors have the ability to deliver a sequence which is devoid of or lacking viral RNA. In a further embodiment a heterologous binding domain (heterologous to gag) located on the RNA to be delivered and a cognate binding domain on gag or pol can be used to ensure packaging of the RNA to be delivered. Both of these vectors are described in WO 2007/072056.

The lentiviral vector may be a "non-primate" vector, i.e., derived from a virus which does not primarily infect primates, especially humans.

The examples of non-primate lentivirus may be any member of the family of lentiviridae which does not naturally infect a primate and may include a feline immunodeficiency virus (FIV), a bovine immunodeficiency virus (BIV), a caprine arthritis encephalitis virus (CAEV), a Maedi visna virus (MVV) or an equine infectious anaemia virus (EIAV).

In a particularly preferred embodiment the viral vector is derived from EIAV. EIAV has the simplest genomic structure of the lentiviruses and is particularly preferred for use in the present invention. In addition to the gag, pol and env genes EIAV encodes three other genes: tat, rev, and S2. Tat acts as a transcriptional activator of the viral LTR (Derse and Newbold (1993); Maury et al. (1994)) and Rev regulates and coordinates the expression of viral genes through rev-response elements (RRE) (Martarano et al. (1994)). The mechanisms of action of these two proteins are thought to be broadly similar to the analogous mechanisms in the primate viruses (Martano et al. ibid). The function of S2 is unknown. In addition, an EIAV protein, Ttm, has been identified that is encoded by the first exon of tat spliced to the env coding sequence at the start of the transmembrane protein.

Preferred vectors of the present invention are recombinant lentiviral vectors.

The term "recombinant lentiviral vector" refers to a vector with sufficient lentiviral genetic information to allow packaging of an RNA genome, in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell. A recombinant lentiviral vector is incapable of independent replication to produce infectious lentiviral particles within the final target cell. Usually the recombinant lentiviral vector lacks a functional gag-pol and/or env gene and/or other genes essential for replication. The vector of the present invention may be configured as a split-intron vector. A split intron vector is described in PCT patent application WO 99/15683.

Preferably the recombinant lentiviral vector of the present invention has a minimal viral genome.

As used herein, the term "minimal viral genome" means that the viral vector has been manipulated so as to remove the non-essential elements and to retain the essential elements in order to provide the required functionality to infect, transduce and deliver a nucleotide sequence of interest to a target host cell. Further details of this strategy can be found in our WO 98/17815.

In one embodiment of the present invention, the vector is a self-inactivating vector.

By way of example, self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al. (1986) Proc. Natl. Acad. Sci. 83:3194-3198; Dougherty and Temin (1987) Proc. Natl. Acad. Sci. 84:1197-1201; Hawley et al. (1987) Proc. Natl. Acad. Sci. 84:2406-2410; Yee et al. (1987) Proc. Natl. Acad. Sci. 91:9564-9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al. (1983) Nucleic Acids Res. 11:1855-1872) or suppression of transcription (Emerman and Temin (1984) Cell 39:449-467). This strategy can also be used to eliminate downstream transcription from the 3' LTR into genomic DNA (Herman and Coffin (1987) Science 236:845-848). This is of particular concern in human gene therapy where it is of critical importance to prevent the adventitious activation of an endogenous oncogene.

However, the plasmid vector used to produce the viral genome within a host cell/packaging cell will also include transcriptional regulatory control sequences operably linked to the lentiviral genome to direct transcription of the genome in a host cell/packaging cell. These regulatory sequences may be the natural sequences associated with the transcribed lentiviral sequence, i.e. the 5' U3 region, or they may be a heterologous promoter such as another viral promoter, for example the CMV promoter. Some lentiviral genomes require additional sequences for efficient virus production. For example, in the case of HIV, rev and RRE sequence are preferably included. However the requirement for rev and RRE may be reduced or eliminated by codon optimisation. Further details of this strategy can be found in our WO 01/79518. Alternative sequences which perform the same function as the rev/RRE system are also known. For example, a functional analogue of the rev/RRE system is found in the Mason Pfizer monkey virus. This is known as the constitutive transport element (CTE) and comprises an RRE-type sequence in the genome which is believed to interact with a factor in the infected cell. The cellular factor can be thought of as a rev analogue. Thus, CTE may be used as an alternative to the rev/RRE system. Any other functional equivalents which are known or become available may be relevant to the invention. For example, it is also known that the Rex protein of HTLV-I can functionally replace the Rev protein of HIV-1. It is also known that Rev and Rex have similar effects to IRE-BP.

In a particularly preferred embodiment, the lentiviral vector according to the present invention consists of a self-inactivating minimal lentiviral vector, derived from Equine Infectious Anaemia Virus (EIAV), preferably encoding three enzymes that are involved in the dopamine synthetic pathway. The proteins encoded by such a vector may comprise a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (CH1) gene. The vector may be produced by the transient transfection of cells (e.g. HEK293T cells) with three plasmids, encoding for: (1) the recombinant EIAV ProSavin® (Oxford BioMedica plc, Oxford UK) vector genome (pONYK1-ORT, WO 02/29065 and Farley et al. (2007) J. Gen. Med. 9:345-356), (2) the synthetic EIAV gag/pol expression vector (pESGPK, WO 01/79518, WO 05/29065), (3) the VSV-G envelope expression vector (pHGK)

Packaging Sequence

As utilised within the context of the present invention the term "packaging signal" which is referred to interchangeably as "packaging sequence" or "psi" is used in reference to the non-coding, cis-acting sequence required for encapsidation of lentiviral RNA strands during viral particle formation. In HIV-1, this sequence has been mapped to loci extending from upstream of the major splice donor site (SD) to at least the gag start codon.

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Pseudotyping

Preferably, the retroviral vector according to the present invention has been pseudotyped. In this regard, pseudotyping can confer one or more advantages. For example, with the lentiviral vectors, the env gene product of the HIV based vectors would restrict these vectors to infecting only cells that express a protein called CD4. But if the env gene in these vectors has been substituted with env sequences from other RNA viruses, then they may have a broader infectious spectrum (Verma and Somia (1997)). By way of examples, Miller et al. pseudotyped an MoMLV vector with the envelope from the amphotropic retrovirus 4070A (Mol. Cell. Biol. 5:431-437) other workers have pseudotyped an HIV based vector with the glycoprotein from VSV (Verma and Somia (1997)).

In another alternative, the Env protein may be a modified Env protein such as a mutant or engineered Env protein. Modifications may be made or selected to introduce targeting ability or to reduce toxicity or for another purpose (Valsesia-Wittman et al. (1996); Nilson et al. (1996); Fielding et al. (1998) and references cited therein).

The retroviral vector may be pseudotyped with any molecule of choice, but the VSV-G envelope is particularly preferred.

VSV-G:

The envelope glycoprotein (G) of Vesicular stomatitis virus (VSV), a rhabdovirus, is an envelope protein that has been shown to be capable of pseudotyping certain retroviruses.

Its ability to pseudotype MoMLV-based retroviral vectors in the absence of any retroviral envelope proteins was first shown by Emi et al. (1991) J. Virol. 65:1202-1207). WO 94/294440 teaches that retroviral vectors may be successfully pseudotyped with VSV-G. These pseudotyped VSV-G vectors may be used to transduce a wide range of mammalian cells. More recently, Abe et al. (1998) J. Virol. 72(8) 6356-6361 teach that non-infectious retroviral particles can be made infectious by the addition of VSV-G.

Burns et al. (1993) Proc. Natl. Acad. Sci. USA 90:8033-7) successfully pseudotyped the retrovirus MLV with VSV-G and this resulted in a vector having an altered host range compared to MLV in its native form. VSV-G pseudotyped vectors have been shown to infect not only mammalian cells, but also cell lines derived from fish, reptiles and insects (Burns et al. (1993) ibid). They have also been shown to be more efficient than traditional amphotropic envelopes for a variety of cell lines (Yee et al., (1994) Proc. Natl. Acad. Sci. USA 91:9564-9568, Lin, Emi et al. (1991) J. Virol. 65:1202-1207). VSV-G protein can also be used to pseudotype certain lenti and retroviruses because its cytoplasmic tail is capable of interacting with the retroviral cores.

The provision of a non-lentiviral pseudotyping envelope such as VSV-G protein gives the advantage that vector particles can be concentrated to a high titre without loss of infectivity (Akkina et al. (1996) J. Virol. 70:2581-5). Lentivirus and retrovirus envelope proteins are apparently unable to withstand the shearing forces during ultracentrifugation, probably because they consist of two non-covalently linked subunits. The interaction between the subunits may be disrupted by the centrifugation. In comparison the VSV glycoprotein is composed of a single unit. VSV-G protein pseudotyping can therefore offer potential advantages.

WO 00/52188 describes the generation of pseudotyped retroviral vectors, from stable producer cell lines, having vesicular stomatitis virus-G protein (VSV-G) as the membrane-associated viral envelope protein, and provides a gene sequence for the VSV-G protein.

Ross River Virus

The Ross River viral envelope has been used to pseudotype a nonprimate lentiviral vector (FIV) and following systemic administration predominantly transduced the liver (Kang et al. (2002)). Efficiency was reported to be 20-fold greater than obtained with VSV-G pseudotyped vector, and caused less cytotoxicity as measured by serum levels of liver enzymes suggestive of hepatotoxicity.

Ross River Virus (RRV) is an alphavirus spread by mosquitoes which is endemic and epidemic in tropical and temperate regions of Australia. Antibody rates in normal populations in the temperate coastal zone tend to be low (6% to 15%) although sero-prevalence reaches 27 to 37% in the plains of the Murray Valley River system. In 1979 to 1980 Ross River Virus became epidemic in the Pacific Islands. The disease is not contagious between humans and is never fatal, the first symptom being joint pain with fatigue and lethargy in about half of patients (Fields Virology).

Baculovirus GP64

The baculovirus GP64 protein has been shown to be an attractive alternative to VSV-G for viral vectors used in the large-scale production of high-titre virus required for clinical and commercial applications (Kumar M, Bradow B P, Zimmerberg J (2003) Hum. Gene Ther. 14(1):67-77). Compared with VSV-G-pseudotyped vectors, GP64-pseudotyped vectors have a similar broad tropism and similar native titres. Because, GP64 expression does not kill cells, 293T-based cell lines constitutively expressing GP64 can be generated.

Rabies G

In the present invention the vector may be pseudotyped with at least a part of a rabies G protein or a mutant, variant, homologue or fragment thereof.

Teachings on the rabies G protein, as well as mutants thereof, may be found in WO 99/61639 and well as Rose et al. (1982) J. Virol. 43:361-364, Hanham et al. (1993) J. Virol. 67:530-542, Tuffereau et al. (1998) J. Virol. 72:1085-1091, Kucera et al. (1985) J. Virol. 55:158-162, Dietzschold et al. (1983) PNAS 80:70-74, Seif et al. (1985) J. Virol. 53:926-934, Coulon et al. (1998) J. Virol. 72:273-278, Tuffereau et al. (1998) J. Virol. 72:1085-10910, Burger et al. (1991) J. Gen. Virol. 72:359-367, Gaudin et al. (1995) J. Virol. 69:5528-5534, Benmansour et al. (1991) J. Virol. 65:4198-4203, Luo et al. (1998) Microbiol. Immunol. 42:187-193, Coll (1997) Arch. Virol. 142:2089-2097, Luo et al. (1997) Virus Res. 51:35-41, Luo et al. (1998) Microbiol. Immunol. 42:187-193, Coll (1995) Arch. Virol. 140:827-851, Tuchiya et al. (1992) Virus Res. 25:1-13, Morimoto et al. (1992) Virology 189:203-216, Gaudin et al. (1992) Virology 187:627-632, Whitt et al (1991) Virology 185:681-688, Dietzschold et al. (1978) J. Gen. Virol. 40:131-139, Dietzschold et al. (1978) Dev. Biol. Stand. 40:45-55, Dietzschold et al. (1977) J. Virol. 23:286-293, and Otvos et al. (1994) Biochim. Biophys. Acta 1224:68-76. A rabies G protein is also described in EP 0445625.

Alternative Envelopes

Other envelopes which can be used to pseudotype retroviral vectors include Mokola, Ebola, 4070A and LCMV (lymphocytic choriomeningitis virus).

Nucleotide of Interest (NOI)

In one embodiment, the virus according to the invention is a wild type retroviral vector, or a mutant or part thereof that is still infectious in cells according to the invention. In another embodiment, the virus is a recombinant retroviral vector comprising heterologous information, which may be used in a therapeutic setting for gene therapy purposes, or as an antigen for vaccination purposes. This is a preferred embodiment using for instance retroviral vectors. The heterologous information is referred to as 'nucleotide of interest' (NOI).

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, microRNA, shRNA, siRNA, ribozymes, a transdomain negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group). The NOIs may also encode pro-drug activating enzymes.

In another embodiment, the NOI may be useful in the treatment of a neurodegenerative disorder.

In another embodiment, the NOI may be useful in the treatment of Parkinson's disease.

In yet another embodiment, the NOI may encode an enzyme or enzymes involved in dopamine synthesis. For example, the enzyme may be one or more of the following: tyrosine hydroxylase, GTP-cyclohydrolase I and/or aromatic amino acid dopa decarboxylase. The sequences of all three genes are available: GenBank® Accession Nos. X05290, U19523 and M76180 respectively.

Alternatively the NOI may encode the vesicular monoamine transporter 2 (VMAT2). In an alternative embodiment the viral genome comprises an NOI encoding aromatic amino acid dopa decarboxylase and an NOI encoding VMAT 2. Such a genome may be used in the treatment of Parkinson's disease, in particular in conjunction with peripheral administration of L-DOPA.

In another embodiment the NOI may encode a therapeutic protein or combination of therapeutic proteins.

In another embodiment, the NOI may encode a protein or proteins selected from the group consisting of glial cell derived neurotophic factor (GDNF), brain derived neurotrophic factor (BDNF), ciliary neurotrophic factor (CNTF), neurotrophin-3 (NT-3), acidic fibroblast growth factor (aFGF), basic fibroblast growth factor (bFGF), interleukin-1 beta (IL-1β), tumor necrosis factor alpha (TNF-α), insulin growth factor-2, VEGF-A, VEGF-B, VEGF-C/VEGF-2, VEGF-D, VEGF-E, PDGF-A, PDGF-B, hetero- and homo-dimers of PDFG-A and PDFG-B In another embodiment, the NOI may encode an anti-angiogenic protein or anti-angiogenic proteins selected from the group consisting of angiostatin, endostatin; platelet factor 4, pigment epithelium derived factor (PEDF), restin, interferon-alpha, interferon-inducible protein, gro-beta and tubedown-1, Interleukin (IL)-1, IL-12, retinoic acid, anti-VEGF antibodies, aptamers, antisense oligos, siRNA, thrombospondin, VEGF receptor proteins such as those described in U.S. Pat. Nos. 5,952,199 and 6,100,071, and anti-VEGF receptor antibodies.

In another embodiment the NOI may encode a protein normally expressed in an ocular cell.

In another embodiment, the NOI may encode a protein normally expressed in a photoreceptor cell.

In another embodiment, the NOI may encode a protein selected from the group comprising RPE65, arylhydrocarbon-interacting receptor protein like 1 (AIPL1), CRB1, lecithin retinal acetyltransferace (LRAT), photoreceptor-specific homeo box (CRX), retinal guanylate cyclise (GUCY2D), RPGR interacting protein 1 (RPGRIP1), LCA2, LCA3, LCAS, dystrophin, PRPH2, CNTF, ABCR/ABCA4, EMP1, TIMP3, MERTK, ELOVL4, MYO7A, USH2A, and opticin.

Thus, the retroviral vector according to the present invention may be used to deliver one or more NOI(s) useful in the treatment of the disorders listed in WO 98/05635, WO 98/07859, WO 98/09985. The nucleotide of interest may be DNA or RNA. Examples of such diseases are given below:

A disorder which responds to cytokine and cell proliferation/differentiation activity; immunosuppressant or immunostimulant activity (e.g. for treating immune deficiency, including infection with human immune deficiency virus;

regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells.

Malignancy disorders including cancer, benign and malignant tumour growth, invasion and spread, angiogenesis, metastases, ascites and malignant pleural effusion.

Autoimmune diseases including arthritis, including rheumatoid arthritis, hypersensitivity, allergic reactions, asthma, systemic lupus erythematosus, collagen diseases and other diseases.

Cardiovascular diseases including arteriosclerosis, atherosclerotic heart disease, reperfusion injury, cardiac arrest, myocardial infarction, vascular inflammatory disorders, respiratory distress syndrome, cardiovascular effects, migraine and aspirin-dependent anti-thrombosis, stroke, cerebral ischaemia, ischaemic heart disease or other diseases.

Diseases of the gastrointestinal tract including peptic ulcer, ulcerative colitis, Crohn's disease and other diseases.

Hepatic diseases including hepatic fibrosis, liver cirrhosis or other diseases.

Renal and urologic diseases including thyroiditis or other glandular diseases, glomerulonephritis or other diseases.

Ear, nose and throat disorders including otitis or other oto-rhino-laryngological diseases, dermatitis or other dermal diseases.

Dental and oral disorders including periodontal diseases, periodontitis, gingivitis or other dental/oral diseases.

Testicular diseases including orchitis or epididimo-orchitis, infertility, orchidal trauma or other testicular diseases.

Gynaecological diseases including placental dysfunction, placental insufficiency, habitual abortion, eclampsia, pre-eclampsia, endometriosis and other gynaecological diseases.

Ophthalmologic disorder such as posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, macular degeneration including age related macular degeneration (AMD) and juvenile macular degeneration including Best Disease, Stargardt's Disease, Usher's syndrome, Doyne's honeycomb retinal dystrophy, Sorby's Macular Dystrophy, Juvenile retinoschisis, Cone-Rod Dystrophy, Corneal Dystrophy, Fuch's Dystrophy, Leber's congenital amaurosis, Leber's hereditary optic neuropathy (LHON), Adie syndrome, Oguchi disease, degenerative fondus disease, ocular trauma, ocular inflammation caused by infection, proliferative vitreo-retinopathies, acute ischaemic optic neuropathy, excessive scarring, e.g. following glaucoma filtration operation, reaction against ocular implants, corneal transplant graft rejection, and other ophthalmic diseases.

Neurological and neurodegenerative disorders including Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, strokes, post-polio syndrome, psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chorea, myasthenia gravis, pseudo-tumour cerebri, Down's Syndrome, Huntington's disease, CNS compression or CNS trauma or infections of the CNS, muscular atrophies and dystrophies, diseases, conditions or disorders of the central and peripheral nervous systems, motor neuron disease including amyotropic lateral sclerosis, spinal muscular atropy, spinal cord and avulsion injury.

Other diseases and conditions such as post-traumatic inflammation, haemorrhage, coagulation and acute phase response, cachexia, anorexia, acute infection, septic shock, infectious diseases, complications or side effects of surgery, bone marrow transplantation or other transplantation complications and/or side effects, complications and side effects of gene therapy, e.g. due to infection with a viral carrier, or AIDS, to suppress or inhibit a humoral and/or cellular immune response, for the prevention and/or treatment of graft rejection in cases of transplantation of natural or artificial cells, tissue and organs such as cornea, bone marrow, organs, lenses, pacemakers, natural or artificial skin tissue.

siRNA/micro-RNA

The NOI may comprise or encode a siRNA or micro-RNA or shRNA or regulated micro or shRNA (Dickins et al. (2005) Nature Genetics 37: 1289-1295, Silva et al. (2005) Nature Genetics 37:1281-1288).

Post-transcriptional gene silencing (PTGS) mediated by double-stranded RNA (dsRNA) is a conserved cellular defence mechanism for controlling the expression of foreign genes. It is thought that the random integration of elements such as transposons or viruses causes the expression of dsRNA which activates sequence-specific degradation of homologous single-stranded mRNA or viral genomic RNA. The silencing effect is known as RNA interference (RNAi) (Ralph et al. (2005) Nature Medicine 11:429-433). The mechanism of RNAi involves the processing of long dsRNAs into duplexes of about 21-25 nucleotide (nt) RNAs. These products are called small interfering or silencing RNAs (siRNAs) which are the sequence-specific mediators of mRNA degradation. In differentiated mammalian cells dsRNA>30 bp has been found to activate the interferon response leading to shut-down of protein synthesis and non-specific mRNA degradation (Stark et al. (1998)). However this response can be bypassed by using 21 nt siRNA duplexes (Elbashir et al. (2001), Hutvagner et al. (2001)) allowing gene function to be analysed in cultured mammalian cells.

In another embodiment the NOI comprises a micro-RNA. Micro-RNAs are a very large group of small RNAs produced naturally in organisms, at least some of which regulate the expression of target genes. Founding members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme.

Promoters

Expression of a NOI may be controlled using control sequences, which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters.

Suitable promoting sequences are strong promoters including those derived from the genomes of viruses—such as polyoma virus, adenovirus, fowlpox virus, bovine papilloma virus, avian sarcoma virus, cytomegalovirus (CMV), retrovirus and Simian Virus 40 (SV40)—or from heterologous mammalian promoters—such as the actin promoter or ribosomal protein promoter. Transcription of a gene may be increased further by inserting an enhancer sequence into the vector. Enhancers are relatively orientation and position independent; however, one may employ an enhancer from a eukaryotic cell virus—such as the SV40 enhancer on the late side of the replication origin (bp 100-270) and the CMV early promoter enhancer. The enhancer may be spliced into the vector at a position 5' or 3' to the promoter, but is preferably located at a site 5' from the promoter.

The promoter can additionally include features to ensure or to increase expression in a suitable host. For example, the features can be conserved regions e.g. a Pribnow Box or a TATA box. The promoter may even contain other sequences to affect (such as to maintain, enhance, decrease) the levels of expression of a nucleotide sequence. Suitable other sequences include the Shl-intron or an ADH intron. Other sequences include inducible elements—such as temperature, chemical, light or stress inducible elements. Also, suitable elements to enhance transcription or translation may be present.

Codon Optimisation

The polynucleotides used in the present invention (including the NOI and/or vector components) may be codon optimised. Codon optimisation has previously been described in WO 99/41397 and WO 01/79518. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of a gene of interest, e.g. a NOI or packaging components in mammalian producer cells, can be achieved. Codon usage tables are known in the art for mammalian cells, as well as for a variety of other organisms.

Codon optimisation of viral vector components has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. In lentiviral vectors codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with some exceptions, for example the sequence encompassing the frameshift site of gag-pol (see below).

The gag-pol gene comprises two overlapping reading frames encoding the gag-pol proteins. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 by fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In one embodiment, codon optimisation is based on lightly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variant may be used to enhance particular parts of the transduction process. Examples of HIV-1 variants may be found at the HIV Databases operated by Los Alamos National Security, LLC. Details of EIAV clones may be found at the National Center for Biotechnology Information (NCBI) database.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the lentiviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

Retroviral Vector Production Systems

Retroviral vectors can be suitably propagated in cells (sometimes referred to as 'host cells').

A cell according to the present invention can be any cell wherein a desired retroviral vector can be propagated.

By using stable producer/packaging cell lines, it is possible to propagate quantities of viral vector particles (e.g. to prepare suitable titres of the lentiviral vector) for subsequent purification.

As used herein, the term "producer cell" or "vector producing cell" refers to a cell which contains all the elements necessary for production of lentiviral vector particles.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as codon optimised gag-pol and env) but they do not contain a packaging signal.

Preferably producer cells/packaging cells according to the present invention are derived from a mammalian cell and, preferably, from a primate cell such as human embryonic kidney cell which is particularly preferred. Although primate cells are preferred, any type of cell that is capable of supporting replication of the virus would be acceptable in the practice of the invention. Other cell types might include, but are not limited to any eukaryotic cells for which tissue culture techniques are established as long as the cells are retrovirus permissive.

The cell may be derived from an existing cell line, e.g., from a HEK 293 cell line In order to improve safety, cell lines have been produced wherein the 3'LTR of the provirus is deleted. In such cells, two recombinations would be necessary to produce a wild type virus. A further improvement involves the introduction of the gag-pol genes and the env gene on separate constructs. These constructs can be introduced sequentially to prevent recombination during transfection. In these split-construct cell lines, a further reduction in recombination may be achieved by changing the codons. This technique, based on the redundancy of the genetic code, aims to reduce homology between the separate constructs, for example between the regions of overlap in the gag-pol and env open reading frames.

In one embodiment vector production cells used in the present invention use as their production system, three transcription units expressing a genome, the gag-pol components and an envelope. The envelope expression cassette may include one of a number of envelopes such as VSV-G or various murine retrovirus envelopes such as 4070A. The VSV-G envelope is particularly preferred.

In one embodiment the envelope protein sequences and nucleocapsid sequences are all stably integrated in the producer and/or packaging cell. However, one or more of these sequences could also exist in episomal form and gene expression could occur from the episome.

A further embodiment utilises an inducible system for example the Tet system (Gossen and Bujard) to generate stable producer/packaging cells which express a toxic gene product such as VSV-G (EP 0572401B).

In an alternative embodiment transient transfection is used to generate the viral producing cells of the present invention. Transient transfection avoids the longer time required to generate stable vector-producing cell lines and can be used if the vector genome or lentiviral packaging components are toxic to cells.

In a particularly preferred embodiment, the packaging cell used to produce the retroviral vector of the present invention is produced by the transfection of cells (e.g HEK293T cells) with three plasmids encoding for (i) the recombinant retroviral vector genome, (ii) an expression vector encoding gag/pol and (iii) an expression vector encoding env.

The transfection methods may be performed using methods well known in the art. For example, the transfection process may be performed using calcium phosphate or commercially available formulations such as Lipofectamine™ 2000 CD (Invitrogen, CA) or polyethylenimine (PEI).

Packaging/producer cells can also be generated by transducing a suitable cell line with a retroviral vector which expresses one of the components of the packaging/producer cell, i.e. a genome, the gag-pol components and an envelope as described in WO 2004/022761.

Cells transfected with the retroviral vector encoding components are cultured to increase cell and virus numbers and/or virus titre s. Culturing a cell is done to enable it to metabolize, and/or grow and/or divide and/or produce virus of interest according to the invention. This can be accomplished by methods well known to persons skilled in the art, and includes but is not limited to providing nutrients for the cell, for instance in the appropriate culture media. The methods may comprise growth adhering to surfaces, growth in suspension, or combinations thereof. Culturing can be done for instance in tissue culture flasks, dishes, roller bottles or in bioreactors, using batch, fed-batch, continuous systems, hollow fiber, and the like. In order to achieve large scale (continuous) production of virus through cell culture it is preferred in the art to have cells capable of growing in suspension. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9).

Preferably cells are initially 'bulked up' in tissue culture flasks and subsequently grown in multilayered culture vessels to generate the vector producing cells of the present invention.

Preferably cells are grown in an adherent mode to generate the vector producing cells of the present invention.

Preferably cells are grown in a batch mode to generate the vector producing cells of the present invention.

Clarification

In preferred embodiments of the invention, the supernatant harvested from the cell culture is clarified.

According to certain preferred embodiments the clarification step is performed before the addition of nuclease.

Clarification may be done by a filtration step, removing cell debris and other impurities. Suitable filters may utilize cellulose filters, regenerated cellulose fibers, cellulose fibers combined with inorganic filter aids (e.g. diatomaceous earth, perlite, fumed silica), cellulose filters combined with inorganic filter aids and organic resins, or any combination thereof, and polymeric filters (examples include but are not limited to nylon, polypropylene, polyethersulfone) to achieve effective removal and acceptable recoveries. In general, a multiple stage process is preferable but not required. An exemplary two or three-stage process would consist of a coarse filter(s) to remove large precipitate and cell debris followed by polishing second stage filter(s) with nominal pore sizes greater than 0.2 micron but less than 1 micron. The optimal combination may be a function of the precipitate size distribution as well as other variables. In addition, single stage operations employing a relatively small pore size filter or centrifugation may also be used for clarification. More generally, any clarification approach including but not limited to dead-end filtration, microfiltration, centrifugation, or body feed of filter aids (e.g. diatomaceous earth) in combination with dead-end or depth filtration, which provides a filtrate of suitable clarity to not foul the membrane and/or resins in the subsequent steps, will be acceptable to use in the clarification step of the present invention.

In one embodiment, depth filtration and membrane filtration is used. Commercially available products useful in this regard are for instance mentioned in WO 03/097797, p. 20-21. Membranes that can be used may be composed of different materials, may differ in pore size, and may be used in combinations. They can be commercially obtained from several vendors.

Preferably the filter used for clarification is in the range of 1.2 to 0.22 µm.

More preferably the filter used for clarification is either a 1.2/0.45 µm filter or an asymmetric filter with a minimum nominal pore size of 0.22 µm Nuclease Treatment The present invention in preferred embodiments employs nuclease to degrade contaminating DNA/RNA, i.e. mostly host cell nucleic acids. Exemplary nucleases suitable for use in the present invention include Benzonase® Nuclease (EP 0229866) which attacks and degrades all forms of DNA and RNA (single stranded, double stranded linear or circular) or any other DNase and/or RNase commonly used within the art for the purpose of eliminating unwanted or contaminating DNA and/or RNA from a preparation. In preferred embodiments, the nuclease is Benzonase® Nuclease, which rapidly hydrolyzes nucleic acids by hydrolyzing internal phosphodiester bonds between specific nucleotides, thereby reducing the size of the polynucleotides in the vector containing supernatant. Benzonase® Nuclease can be commercially obtained from Merck KGaA (code W214950). The concentration in which the nuclease is employed is preferably within the range of 1-100 units/ml.

According to certain preferred embodiments more than one nuclease treatment is included. For example, Benzonase® Nuclease could be added to the vector-containing supernatant before and/or after the vector is purified by chromatography.

As a non-limiting example, Benzonase® Nuclease is added to the vector-containing supernatant which is between 37° C. and ambient temperature and then the mixture is incubated at 2 to 8° C., preferably overnight.

Instead of or in addition to treating with a nuclease to fragment free nucleic acid (mainly host cell DNA), selective precipitation (removal) of impurity DNA in cell culture medium might be applied, e.g. by precipitation with an appropriate amount of a selective precipitation agent such as domiphen bromide (DB), CTAB (cetyl trimethylammonium bromide), cetylpyridinium chloride (CPC), benzethonium chloride (BTC), tetradecyltrimethyl-ammonium chloride (TTA), polyethylene imine (PEI), etc., as disclosed in detail in WO 03/097797.

Ultrafiltration/Diafiltration

According to embodiments of the present invention, the vector suspension is subjected to ultrafiltration (sometimes referred to as diafiltration when used for buffer exchange) at least once during the process, e.g. for concentrating the vector and/or buffer exchange. The process used to concentrate the vector according to the method of the present invention can include any filtration process (e.g., ultrafiltration (UF)) where the concentration of vector is increased by forcing diluent to be passed through a filter in such a manner that the diluent is removed from the vector preparation whereas the vector is unable to pass through the filter and thereby remains, in concentrated form, in the vector preparation. UF is described in detail in, e.g., Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration ("TFF") as described in, e.g., MILLIPORE catalogue entitled "Pharmaceutical Process Filtration Catalogue" pp. 177-202 (Bedford, Mass., 1995/96). TFF is widely used in the bioprocessing industry for cell harvesting, clarification, purification and concentration of products including viruses. The system is composed of three distinct process streams: the feed solution, the permeate and the retentate. Depending on application, filters with different pore sizes may be used. In the present invention the retentate contains the product (lentiviral vector). Hereto, the particular ultrafiltration membrane selected will have a pore size sufficiently small to retain vector but large enough to effectively clear impurities. Depending on the manufacturer and membrane type, for retroviral vectors nominal molecular weight cutoffs (NMWC) between 100 and 1000 kDa may be appropriate, for instance membranes with 300 kDa or 500 kDa NMWC. The membrane composition may be, but is not limited to, regenerated cellulose, polyethersulfone, polysulfone, or derivatives thereof. The membranes can be flat sheets (also called flat screens) or hollow fibers. A preferred UF used in the present invention is hollow fibre UF. UF is generally referred to filtration using filters with a pore size of smaller than 0.1 µm. Products are generally retained, while volume can be reduced through permeation (or be kept constant during diafiltration by adding buffer with the same speed as the speed with which the permeate, containing buffer and impurities, is removed at the permeate side).

The two most widely used geometries for TFF in the biopharmaceutical industry are plate & frame (flat screens) and hollow fiber modules. Hollow fiber units for ultrafiltration and microfiltration were developed by Amicon and Ramicon in the early 1970s (Cheryan, M. Ultrafiltration Handbook), even though now there are multiple vendors including Spectrum and GE Healthcare. The hollow fiber modules consist of an array of self-supporting fibers with a dense skin layer. Fiber diameters range from 0.5 mm-3 mm. An advantage of hollow fiber modules is the availability of filters from small membrane areas (ca. 16 cm$^2$) to very large membrane areas (ca. 20 m$^2$) allowing linear and simple scale-up. In certain preferred embodiments according to the invention, hollow fibers are used for TFF. These are reported to give less shear and a better viral particle/infectious unit (VP/IU) ratio than flat screen membranes. Further, the trans membrane pressure is generally lower in hollow fibers than with flat screens. In certain embodiments, hollow fibers of 500 kDa (0.05 µm) pore size are used according to the invention. Ultrafiltration may comprise diafiltration (DF), using ultrafilters and is an ideal way for removal and exchange of salts, sugars, non-aqueous solvents, separation of free from bound species, removal of material of low molecular weight, or rapid change of ionic and/or pH environments. Microsolutes are removed most efficiently by adding solvent to the solution being ultrafiltered at a rate equal to the UF rate. This washes microspecies from the solution at a constant volume, purifying the retained vector.

UF/DF can be used to concentrate and/or buffer exchange the vector suspensions according to the present invention in different stages of the purification process. The present invention preferably utilizes a DF step to exchange the buffer of the supernatant after chromatography or other purification steps, but may also be used prior to chromatography.

Preferably, the eluate from the chromatography step according to the present invention is concentrated and further purified by ultrafiltration-diafiltration. During this process the vector is exchanged into formulation buffer. However, it has surprisingly been found that improved vector production can be achieved if concentration to the final desired concentration does not take place until after the filter-sterilisation step. After said sterile filtration, the filter sterilised substance is concentrated by aseptic UF to produce the bulk vector product.

In embodiments of the invention the ultrafiltration/diafiltration may be tangential flow diafiltration, stirred cell diafiltration and dialysis.

Chromatography

Purification techniques are well known to those of skill in the art. These techniques tend to involve the separation of the vector particles from the cellular milieu and, if necessary, the further purification of the vector particles. One or more of a variety of chromatographic methods may be used for this purification. Although ion exchange, and more particularly anion exchange, chromatography is a preferred method for the present invention, other methods could be used. A description of some of the relevant chromatographic techniques is given below.

Ion-Exchange Chromatography

Ion-exchange chromatography utilises the fact that charged species, such as biomolecules and viral vectors, can bind reversibly to a stationary phase (such as a membrane, or else the packing in a column) that has, fixed on its surface, groups that have an opposite charge. There are two types of ion exchangers. Anion exchangers are stationary phases that bear groups having a positive charge and hence can bind species with a negative charge. Cation exchangers bear groups with a negative charge and hence can bind species with positive charge. The pH of the medium has an important influence on this, as it can alter the charge on a species. Thus, for a species such as a protein, if the pH is above the pI, the net charge will be negative, whereas below the pI, the net charge will be positive.

Displacement (elution) of the bound species can be effected by the use of suitable buffers. Thus commonly the ionic concentration of the buffer is increased until the species is displaced through competition of buffer ions for the ionic sites on the stationary phase. An alternative method of elution entails changing the pH of the buffer until the net charge of the species no longer favours biding to the stationary phase. An example would be reducing the pH until the species assumes a net positive charge and will no longer bind to an anion exchanger.

Some purification can be achieved if impurities are uncharged, or else if they bear a charge of opposite sign to that of the desired species, but the same sign to that on the ion exchanger. This is because uncharged species and those having a charge of the same sign to that an ion exchanger, will not normally bind. For different bound species, the strength of the binding varies with factors such as the charge density and the distribution of charges on the various species. Thus by applying an ionic or pH gradient (as a continuous gradient, or as a series of steps), the desired species might be eluted separately from impurities.

Size-Exclusion Chromatography

Size exclusion chromatography is a technique that separates species according to their size. Typically it is performed by the use of a column packed with particles having pores of a well-defined size. For the chromatographic separation, particles are chosen that have pore sizes that are appropriate with regard to the sizes of the species in the mixture to be separated. When the mixture is applied, as a solution (or suspension, in the case of a virus), to the column and then eluted with buffer, the largest particles will elute first as they have limited (or no) access to the pores. Smaller particles will elute later as they can enter the pores and hence take a longer path through the column. Thus in considering the use of size exclusion chromatography for the purification of viral vectors, it would be expected that the vector would be eluted before smaller impurities such as proteins.

Hydrophobic Interaction Chromatography (HIC)

Species, such as proteins, have on their surfaces, hydrophobic regions that can bind reversibly to weakly hydrophobic sites on a stationary phase. In media having a relatively high salt concentration, this binding is promoted. Typically in HIC the sample to be purified is bound to the stationary phase in a high salt environment. Elution is then achieved by the application of a gradient (continuous, or as a series of steps) of decreasing salt concentration. A salt that is commonly used is ammonium sulphate. Species having differing levels of hydrophobicity will tend to be eluted at different salt concentrations and so the target species can be purified from impurities. Other factors, such as pH, temperature and additives to the elution medium such as detergents, chaotropic salts and organics can also influence the strength of binding of species to HIC stationary phases. One, or more, of these factors can be adjusted or utilised to optimise the elution and purification of product.

Viral vectors have on their surface, hydrophobic moieties such as proteins, and thus HIC could potentially be employed as a means of purification.

Reversed-Phase Chromatography (RPC)

Like HIC, RPC separates species according to differences in their hydrophobicities. A stationary phase of higher hydrophobicity than that employed in HIC is used. The stationary phase often consists of a material, typically silica, to which are bound hydrophobic moieties such as alkyl groups or phenyl groups. Alternatively the stationary phase might be an organic polymer, with no attached groups. The sample-containing the mixture of species to be resolved is applied to the stationary phase in an aqueous medium of relatively high polarity which promotes binding. Elution is then achieved by reducing the polarity of the aqueous medium by the addition of an organic solvent such as isopropanol or acetonitrile. Commonly a gradient (continuous, or as a series of steps) of increasing organic solvent concentration is used and the species are eluted in order of their respective hydrophobicities.

Other factors, such as the pH of the elution medium, and the use of additives, can also influence the strength of binding of species to RPC stationary phases. One, or more, of these factors can be adjusted or utilised to optimise the elution and purification of product. A common additive is trifluororacetic acid (TFA). This suppresses the ionisation of acidic groups such as carboxyl moieties in the sample. It also reduces the pH in the eluting medium and this suppresses the ionisation of free silanol groups that may be present on the surface of stationary phases having a silica matrix. TFA is one of a class of additives known as ion pairing agents. These interact with ionic groups, present on species in the sample, that bear an opposite charge. The interaction tends to mask the charge, increasing the hydrophobicity of the species. Anionic ion pairing agents, such as TFA and pentafluoropropionic acid interact with positively charged groups on a species. Cationic ion pairing agents such, as triethylamine, interact with negatively charged groups.

Viral vectors have on their surface, hydrophobic moieties such as proteins, and thus RPC, potentially, could be employed as a means of purification. In considering its use, however, care would be required to limit damage to the vector due to the use of organic solvents and also the low pH conditions often used in the technique.

Affinity Chromatography

Affinity chromatography utilises the fact that certain ligands that bind specifically with biomolecules such as proteins or nucleotides, can be immobilised on a stationary phase. The modified stationary phase can then be used to separate the relevant biomolecule from a mixture. Examples of highly specific ligands are antibodies, for the purification of target antigens and enzyme inhibitors for the purification of enzymes. More general interactions can also be utilised such as the use of the protein A ligand for the isolation of a wide range of antibodies.

Typically, affinity chromatography is performed by application of a mixture, containing the species of interest, to the stationary phase that has the relevant ligand attached. Under appropriate conditions this will lead to the binding of the species to the stationary phase. Unbound components are then washed away before an eluting medium is applied. The eluting medium is chosen to disrupt the binding of the ligand to the target species. This is commonly achieved by choice of an appropriate ionic strength, pH or by the use of substances that will compete with the target species for ligand sites. For some bound species, a chaotropic agent such as urea is used to effect displacement from the ligand. This, however, can result in irreversible denaturation of the species.

Viral vectors have on their surface, moieties such as proteins, that might be capable of binding specifically to appropriate ligands. This means that, potentially, affinity chromatography could be used in their isolation.

Immobilised Metal Ion Affinity Chromatography (IMAC)

Biomolecules, such as proteins, can have on their surface, electron donating moieties that can form coordinate bonds with metal ions. This can facilitate their binding to stationary phases carrying immobilised metal ions such as $Ni^{2+}$, $Cu^{2+}$, $Zn^{2+}$ or $Fe^{3+}$. The stationary phases used in IMAC have chelating agents, typically nitriloacetic acid or iminodiacetic acid covalently attached to their surface and it is the chelating agent that holds the metal ion. It is necessary for the chelated metal ion to have at least one coordination site left available to form a coordinate bond to a biomolecule. Potentially there are several moieties on the surface of biomolecules that might be capable of bonding to the immobilised metal ion. These include histidine, tryptophan and cysteine residues as well as phosphate groups. For proteins, however, the predominant donor appears to be the imidazole group of the histidine residue. Native proteins can be separated using IMAC if they exhibit suitable donor moieties on their surface. Otherwise IMAC can be used for the separation of recombinant proteins bearing a chain of several linked histidine residues.

Typically, IMAC is performed by application of a mixture, containing the species of interest, to the stationary phase. Under appropriate conditions this will lead to the coordinate bonding of the species to the stationary phase. Unbound components are then washed away before an eluting medium is applied. For elution, gradients (continuous, or as a series of steps) of increasing salt concentration or decreasing pH may be used. Also a commonly used procedure is the application of a gradient of increasing imidazole concentration. Biomolecules having different donor properties, for example having histidine residues in differing environments, can be separated by the use of gradient elution.

Viral vectors have on their surface, moieties such as proteins, that might be capable of binding to IMAC stationary phases. This means that, potentially, IMAC could be used in their isolation.

Centrifugation

Suitable centrifugation techniques include zonal centrifugation, isopycnic ultra and pelleting centrifugation.

Filter-Sterilisation

Filter-sterilisation is common in processes for pharmaceutical grade materials, and known to the person skilled in the art. Filter-sterilisation renders the resulting formulation substantially free of contaminants. The level of contaminants following filter-sterilisation is such that the formulation is suitable for clinical use. According to the present invention, any further concentration (e.g. by ultrafiltration) following the filter-sterilisation step is preferably performed in aseptic conditions.

Suitable sterilising filters for use in the present invention are well known to those skilled in the art. Preferably the sterilising filter has a maximum pore size of 0.22 μm Verifying Vector Integrity Various assays may be used to verify the genetic integrity of the retroviral vector during the purification process. One such method is confirming the presence of a gene encoded by the vector. In a preferred embodiment, the method may confirm the presence of one or more nucleotide of interests (NOI) encoded by the vector. This may be achieved by, for example, isolation of RNA from the vector preparation, and digestion with DNaseI to degrade residual plasmid DNA. Reverse transcriptase (RT) reactions convert the RNA to cDNA sequences, and these are followed by specific PCR amplification of selected regions of the NOI sequence.

Pharmaceutical Compositions and Administration

The present invention provides a formulation (pharmaceutical composition) for treating an individual by gene therapy, wherein the composition comprises a therapeutically effective amount of a vector. The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise, or in addition to, the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the composition can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly intracranially, intraoccularly or subcutaneously. For parenteral administration, the compositions may be best used in the form of a sterile aqueous solution which may contain other substances, for example enough salts or monosaccharides to make the solution isotonic with blood. For buccal or sublingual administration, the compositions may be administered in the form of tablets or lozenges which can be formulated in a conventional manner Treatment The retroviral vector produced by the process of the present invention may be used in treatment. It is to be appreciated that all references herein to treatment include curative, palliative and prophylactic treatment. The treatment of mammals is particularly preferred. Both human and veterinary treatments are within the scope of the present invention.

In one embodiment, the retroviral vector formulation produced by the process may be used to introduce the three genes that encode for three enzymes of the dopamine synthetic pathway to treat Parkinson's disease. The retroviral vector is a non-replication, self-inactivating minimal lentiviral vector, derived from Equine infectious anaemia virus (EIAV) which may be pseudotyped with VSV-G or an alternative viral envelope protein. The genes carried by the retroviral vector may comprise a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (CH1) gene. The retroviral vector may be produced by the transient transfection of HEK293T cells with three plasmids, encoding for: (1) the recombinant EIAV vector genome (pONYK1-ORT), (2) the synthetic EIAV gag/pol expression vector (pESGPK), (3) the VSV-G envelope expression vector (pHGK). The retroviral vector formulation may be administered by direct injection into the striatum of the brain.

In another embodiment, the retroviral vector formulation produced by the process may be used as a gene therapy product designed to introduce the corrective MYO7A gene to photoreceptors and supporting retinal pigment epithelial (RPE) cells and thereby attenuate or reverse the deterioration in vision which is associated with Usher 1B Syndrome. The retroviral vector is a non-replicating, self-inactivating minimal lentiviral vector derived from the Equine infectious anaemia virus (EIAV) which may be pseudotyped with VSV-G or an alternative viral envelope protein. The gene carried by the retroviral vector is the MYO7A cDNA, which codes for the MYO7A protein (a large gene which is over 100 mb in length). Expression of the large MYO7A protein may be optimised to target RPE and photoreceptors cells by using the novel CMV/MYO7A chimeric promoter which prevents over-expression of this myosin subtype. However, it is also possible that alternative promoters may be used, such as CMV. The retroviral vector formulation may be administered by direct subretinal injection following vitrectomy of the eye.

In another embodiment, the retroviral vector formulation produced by the process may be used to introduce the corrective ATP-binding cassette gene, ABCA4 (also known as ABCR), to photoreceptors and thereby attenuate or reverse the pathophysiology which leads to Stargardt disease. The retroviral vector is a non-replicating, self-inactivating minimal lentiviral vector derived from the Equine infectious anaemia virus (EIAV) which may be pseudotyped with VSV-G or an alternative viral envelope protein. The gene carried by the retroviral vector is the ABCA4 cDNA, which codes for ABCA4 protein. Expression of the ABCA4 protein may be optimised for expression in both rod and cone photoreceptor cells by using a photoreceptor-specific promoter, such as rhodopsin kinase, however, it is also possible that alternative promoters may be used, such as CMV. The retroviral vector formulation may be administered by direct subretinal injection following vitrectomy of the eye.

In another embodiment, the retroviral vector formulation produced by the process may be used as a gene therapy product designed to prevent recurrence of aberrant blood vessel growth in oedema in the eyes of patients with wet-form age-related macular degeneration (AMD). This retroviral vector delivers a gene or genes encoding an anti-angiogenic protein or proteins, such as angiostatin and/or endostatin. The retroviral vector is a non-replicating, self-inactivating minimal lentiviral vector derived from Equine infectious anaemia virus (EIAV) which may be pseudotyped with VSV-G or an alternative viral envelope protein. In one embodiment the retroviral vector expresses human endostatin and angiostatin genes in a bicistronic configuration utilizing an internal ribosome entry site (IRES) for delivery to retinal pigment epithelial cells. Expression of the anti-angiogenic gene(s) may be restricted to the target retinal pigment epithelium by using an RPE-specific promoter such as the vitelliform macular dystrophy 2 (VMD2) promoter, more recently know as the bestrophin promoter, however it is also possible that alternative promoters may be used such as CMV. The retroviral vector formulation may be administered by direct subretinal injection following vitrectomy of the eye.

In yet another embodiment, the retroviral vector formulation produced by the process may be used as a gene therapy product designed to prevent corneal graft rejection as a result of neovascularization by delivery of anti-angiogenic gene(s) to the donor cornea prior to grafting. The retroviral vector is a non-replicating, self-inactivating minimal lentiviral vector derived from Equine infectious anaemia virus (EIAV) which may be pseudotyped with VSV-G or an alternative viral envelope protein. In one embodiment, the retroviral vector will express anti-angiogenic gene(s) such as human endostatin and angiostatin genes in a bicistronic configuration utilizing an internal ribosome entry site (IRES) for ex vivo delivery to corneal grafts. The retroviral vector formulation may be applied to corneal graft tissue ex vivo, and the transduced donor tissue may also be stored prior to transplantation. Expression of the anti-angiogenic gene(s) may be driven by a constitutive promoter such as the CMV promoter, however it is also possible that alternative promoters may be used.

The invention will now be further described by way of the following non-limiting examples which further illustrate the invention, and are not intended, nor should they be interpreted to, limit the scope of the invention.

EXAMPLES

Various preferred features and embodiments of the invention will now be described by way of non-limiting examples with reference to the accompanying Examples.

Description of the Manufacturing Process

ProSavin® is a lentiviral vector, designed to treat Parkinson's disease by delivering three genes that encode for three enzymes of the dopamine biosynthetic pathway.

The ProSavin® vector active substance consists of a self-inactivating minimal lentiviral vector, derived from Equine Infectious Anaemia Virus (EIAV) and pseudotyped with VSV-G, encoding three enzymes that are involved in the dopamine synthetic pathway.

The proteins encoded by the ProSavin® vector are a truncated form of the human tyrosine hydroxylase (TH*) gene (which lacks the N-terminal 160 amino acids involved in feedback regulation of TH), the human aromatic L-amino-acid decarboxylase (AADC), and the human GTP-cyclohydrolase 1 (CH1) gene.

The ProSavin® vector is produced by the transient transfection of HEK293T cells with three plasmids, encoding for: (1) the recombinant EIAV ProSavin® vector genome (pONYK1-ORT), (2) the synthetic EIAV gag/pol expression vector (pESGPK), (3) the VSV-G envelope expression vector (pHGK).

Figure 1:
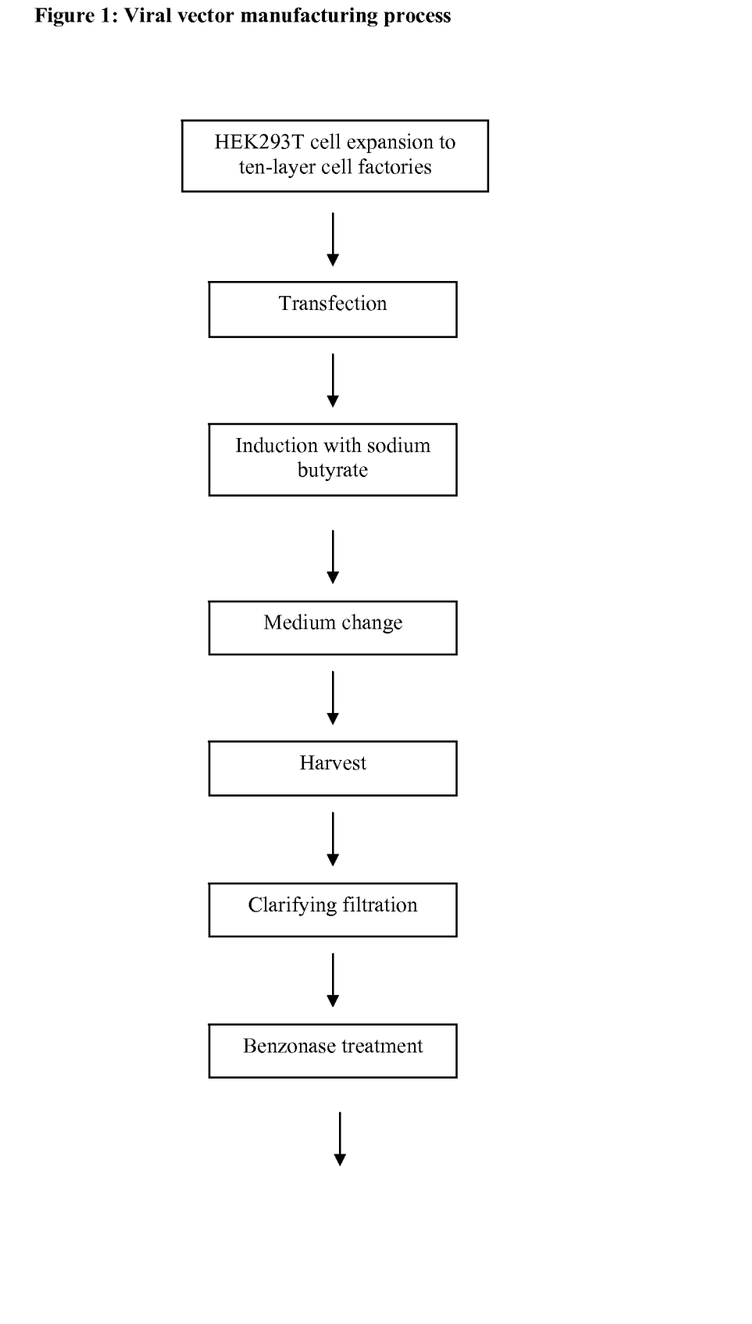
FIG. 1 is a schematic of the retroviral vector production process.

HEK293T cells are expanded in tissue culture flasks, into 10-layer cell factories (CFs) as shown in FIG. 1. The supernatant volume, prior to transfection, is approximately 24 litres. The transfection mixture, containing fixed amounts of the plasmids and Lipofectamine™ 2000 reagent (Invitrogen, CA) CD or PEI is transferred to a reservoir, attached to a cell factory. The culture medium from the CF is drained into the reservoir and, after mixing, the plasmid-containing medium is returned to the CF. This process is repeated for all the CFs. At 14-19 hours post-transfection, the medium is replaced with fresh growth medium supplemented with 10 mM sodium butyrate.

After 6-8 hours of sodium butyrate induction, the sodium butyrate containing medium is replaced by fresh growth medium without sodium butyrate. After a further 21-23 hours, the vector-containing supernatant is harvested into a sterile flexible bag.

Following harvest of the vector-containing supernatant, samples of post production cells are collected from all CFs. The post production cells (PPC) are tested for replication-competent lentivirus (RCL) (see below). The vector-containing supernatant is filter-clarified, using a 1.2/0.45 µm filter and, to digest DNA, Benzonase® Nuclease is added to a final concentration of 5 U/ml (FIG. 1). After overnight incubation at 2-8° C., the Benzonase® Nuclease treated vector is purified by anion exchange membrane chromatography, using a stepwise elution gradient of sodium chloride. The vector-containing fraction of the eluate is then concentrated and further purified by hollow fiber ultrafiltration/diafiltration. During this process the vector is exchanged into formulation buffer to produce drug substance batches of approximately 400 ml, which are aliquoted and stored frozen at ≤−70° C. (FIG. 1).

The drug substance(s) are thawed, pooled and filter-sterilised (0.2 µm). The filter-sterilised bulk drug substance is then concentrated by hollow fiber ultrafiltration to produce the bulk drug product shown in (FIG. 1).

Filter Sterilisation of ProSavin® Vector Preparation

In order to determine the number and concentration of vector particles within individual lots, a real-time reverse transcriptase PCR assay (qRT-PCR) to quantify the number of vector genomic RNA sequences within vector preparations was used. This relies on the predictable nature of retroviral vector RNA packaging and has been described previously (Radcliffe et al. (2008) Gene Therapy 15: 289-297). One EIAV preparation, IH18, had a vector particle concentration at the final product stage of $5.6 \times 10^{12}$ RNA copies per ml. An attempt to filter through a sterilising filtration unit at this concentration led to only 18.5% recovery (total RNA copies were $3.93 \times 10^{13}$ copies prior to filtration and $7.26 \times 10^{12}$ post filtration). Various other preparations had also led to poor filtration recoveries. It was therefore decided to test the hypothesis that filtering at an earlier stage of the process, where the vector particle concentration was lower due to less overall concentration, may lead to higher recoveries from the filtration process. The manufacturing process already included an intermediate hold stage, so filtration studies were focussed on this stage of manufacture for convenience. To test the hypothesis that lower concentrations of vector would lead to improved recovery from the sterilising filtration, material from an earlier vector preparation, which was known to be at a lower particle concentration, was filtered. This lot, IH17, was initially not processed to the 'final product' stage due to losses that had occurred during the ion exchange stage, which led to the lower than expected RNA copy number at an intermediate stage; $5.5 \times 10^{10}$ copies per ml. Filtration of this material led to a dramatically improved recovery of 82.4%. Confirmation that lower concentrations but larger volumes of vector particles led to improved recoveries from the sterilising filtration were subsequently achieved using two different lots, IH19 and IH21. For IH19, the RNA copy number at the intermediate hold stage of manufacture was $1.2 \times 10^{12}$ copies per ml. This was diluted to $4.6 \times 10^{11}$ copies per ml prior to filtration, resulting in a recovery of 84.5% of vector particles (total RNA copies were $9.21 \times 10^{13}$ copies prior to filtration and $7.80 \times 10^{13}$ post filtration). The manufacture of this lot of vector was latterly demonstrated to have been successful by a number of other measures of vector quality, including the vector strength assay. For IH21, the RNA copy number at the intermediate hold stage of manufacture was $8.1 \times 10^{10}$ copies per ml. This was filtered, leading to a recovery of 86.6% of vector particles (total RNA copies were $1.64 \times 10^{13}$ copies prior to filtration and $1.42 \times 10^{13}$ post filtration). The manufacture of this lot of vector was also demonstrated to have been successful by a number of other measures of vector quality, including the vector strength assay.

From these studies, it was concluded that filtration of EIAV particles was achieved with high recoveries when vector concentrations were less than or equal to $4.6 \times 10^{11}$ copies per ml.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

The invention claimed is:

1. A process for producing a sterile lentiviral vector pharmaceutical composition, the process comprising a filter-sterilisation step and a concentration step, wherein the filter-sterilisation step is not the final step in the production process, wherein the filter-sterilisation step occurs prior to the concentration step, wherein the filter-sterilisation step is performed using a sterilising filter with a maximum pore size of 0.2 µm, wherein the concentration step is performed in aseptic conditions, wherein the lentiviral vector pharmaceutical composition comprises a lentiviral vector derived from Equine infectious anaemia virus (EIAV), wherein the lentiviral vector comprises a nucleotide sequence encoding ATP-binding cassette, sub-family A, member 4 (ABCA4) protein or myosin VIIA (MYO7A) protein, and wherein the lentiviral vector pharmaceutical composition is suitable for ex vivo administration or administration to a patient.

2. The process according to claim 1, wherein concentration of the lentiviral vector pharmaceutical composition is performed using an ultrafiltration step.

3. The process according to claim 2, wherein the lentiviral vector comprises a nucleotide sequence encoding ABCA4 protein, and wherein the lentiviral vector pharmaceutical composition is suitable for ex vivo administration or for administration to a patient with Stargardt disease.

4. The process according to claim 2, wherein the lentiviral vector comprises a nucleotide sequence encoding MYO7A protein, and wherein the lentiviral vector pharmaceutical composition is suitable for ex vivo administration or for administration to a patient with Usher syndrome.

5. The process according to claim 1, wherein the lentiviral vector is pseudotyped with envelope glycoprotein of Vesicular stomatisis virus (VSV-G).

6. The process according to claim 1, wherein the lentiviral vector is a non-replicating and/or self-inactivating vector.

7. The process according to claim 1, wherein the nucleotide sequence encoding ABCA4 protein or MYO7A protein is under control of a cytomegalovirus (CMV) promoter.

8. The process according to claim 1, wherein a preparation comprising the lentiviral vector is diluted prior to the filter-sterilisation step.

9. A process for producing a sterile bulk lentiviral vector product, the process comprising the following steps (i) to (vi) in chronological order:
   (i) culturing cells that produce a lentiviral vector, wherein the lentiviral vector is derived from EIAV, and wherein the lentiviral vector comprises a nucleotide sequence encoding ABCA4 protein or MYO7A protein;
   (ii) harvesting the lentiviral vector-containing supernatant;
   (iii) optionally clarifying the supernatant;
   (iv) purifying the lentiviral vector to give a lentiviral vector preparation;
   (v) filter-sterilising the lentiviral vector preparation using a sterilising filter with a maximum pore size of 0.22 µm; and
   (vi) concentrating the lentiviral vector preparation using an ultrafiltration step to produce the bulk lentiviral product, wherein step (vi) is performed under aseptic conditions; and wherein step (vi) is the final step in the process;
   wherein the lentiviral vector preparation is suitable for ex vivo administration or for administration to a patient.

10. The process according to claim 9, wherein step (v) is the penultimate step in the process.

11. The process according to claim 9, wherein the lentiviral vector comprises a nucleotide sequence encoding ABCA4 protein, and wherein the lentiviral vector preparation is suitable for ex vivo administration or for administration to a patient with Stargardt disease.

12. The process according to claim 9, wherein the lentiviral vector comprises a nucleotide sequence encoding MYO7A protein, and wherein the lentiviral vector preparation is suitable for ex vivo administration or for administration to a patient with Usher syndrome.

13. The process according to claim 9, wherein the lentiviral vector is pseudotyped with VSV-G.

14. The process according to claim 9, wherein the lentiviral vector is a non-replicating and/or self-inactivating vector.

15. The process according to claim 9, wherein the nucleotide sequence encoding ABCA4 protein or MYO7A protein is under control of a CMV promoter.

16. The process according to claim 9, wherein the lentiviral vector preparation is diluted prior to filter-sterilisation.

17. The process according to claim 9, wherein step (iii) is performed by filter clarification.

18. The process according to claim 9, wherein step (iv) is performed using a method or combination of methods selected from chromatography, ultrafiltration/diafiltration, and centrifugation.

19. The process according to claim 9, wherein step (iv) includes one or more buffer exchange steps.

20. The process according to claim 19, wherein the buffer exchange comprises exchange of the ultrafiltration/diafiltration retentate with formulation buffer.

21. The process according to claim 9, wherein a nucleic acid degradation step is carried out at any point up to and including step (iv).

* * * * *